(12) United States Patent
Felt (10) Patent No.: US 7,267,690 B2
(45) Date of Patent: Sep. 11, 2007

(54) INTERLOCKED MODULAR DISC NUCLEUS PROSTHESIS

(75) Inventor: Jeffrey C. Felt, Minnetonka, MN (US)

(73) Assignee: Vertebral Technologies, Inc., Minnetonka, MN (US)

( * ) Notice: Subject to any disclaimer, the term of this patent is extended or adjusted under 35 U.S.C. 154(b) by 0 days.

(21) Appl. No.: 11/372,357

(22) Filed: Mar. 9, 2006

(65) Prior Publication Data

US 2006/0293756 A1    Dec. 28, 2006

Related U.S. Application Data

(60) Provisional application No. 60/660,107, filed on Mar. 9, 2005, provisional application No. 60/685,332, filed on May 24, 2005, provisional application No. 60/700,459, filed on Jul. 19, 2005.

(51) Int. Cl.
*A61F 2/44* (2006.01)

(52) U.S. Cl. .................. 623/17.11; 623/17.16

(58) Field of Classification Search ............. 623/14.12, 623/17.11–17.16
See application file for complete search history.

(56) References Cited

U.S. PATENT DOCUMENTS

| | | | |
|---|---|---|---|
| 3,867,728 A | 2/1975 | Stubstad et al. | |
| 4,349,921 A | 9/1982 | Kuntz | |
| 5,047,055 A | 9/1991 | Bao et al. | |
| 5,458,643 A | 10/1995 | Oka et al. | |
| 5,522,899 A | 6/1996 | Michelson | |
| 5,562,736 A | 10/1996 | Ray et al. | |
| 5,674,294 A | 10/1997 | Bainville et al. | |
| 5,702,454 A | 12/1997 | Baumgartner | |
| 5,755,797 A | 5/1998 | Baumgartner | |
| 5,824,093 A | 10/1998 | Ray et al. | |
| 6,110,210 A | 8/2000 | Norton et al. | |
| 6,146,422 A | 11/2000 | Lawson | |
| 6,159,211 A | 12/2000 | Boriani et al. | |
| 6,251,140 B1 | 6/2001 | Marino et al. | |
| 6,258,125 B1 | 7/2001 | Paul et al. | |
| 6,264,695 B1 | 7/2001 | Stoy | |
| 6,371,990 B1 | 4/2002 | Ferree | |
| 6,387,130 B1 | 5/2002 | Stone et al. | |
| 6,419,704 B1 | 7/2002 | Ferree | |
| 6,468,311 B2 * | 10/2002 | Boyd et al. | 623/17.16 |
| 6,488,710 B2 | 12/2002 | Besselink | |
| 6,595,998 B2 * | 7/2003 | Johnson et al. | 606/90 |
| 6,620,196 B1 | 9/2003 | Trieu | |
| 6,652,587 B2 * | 11/2003 | Felt et al. | 623/20.16 |
| 6,726,720 B2 | 4/2004 | Ross et al. | |
| 6,733,535 B2 | 5/2004 | Michelson | |
| 6,764,514 B1 | 7/2004 | Li et al. | |
| 6,855,167 B2 | 2/2005 | Shimp et al. | |
| 6,896,701 B2 | 5/2005 | Boyd et al. | |

(Continued)

*Primary Examiner*—Bruce Snow
*Assistant Examiner*—Cheryl Miller
(74) *Attorney, Agent, or Firm*—Patterson, Thuente, Skaar & Christensen, P.A.

(57) ABSTRACT

A method and apparatus for repairing a damaged intervertebral disc nucleus in a minimally invasive manner utilizes a modular disc prosthesis. The modular disc prosthesis preferably comprises at least three modular segments. In one embodiment, each modular segment includes an inner core and an outer shell. The modular segments are selectively interlockable in situ with each other. The modular segments form an implanted unitary device that closely mimics the geometry of the disc nucleus cavity.

1 Claim, 8 Drawing Sheets

U.S. PATENT DOCUMENTS

| | | |
|---|---|---|
| 2002/0026244 A1 | 2/2002 | Trieu |
| 2003/0055506 A1 | 3/2003 | Stoy et al. |
| 2003/0135279 A1 | 7/2003 | Michelson |
| 2004/0010318 A1 | 1/2004 | Ferree |
| 2004/0019354 A1 | 1/2004 | Johnson et al. |
| 2004/0054413 A1 | 3/2004 | Higham et al. |
| 2004/0064144 A1 | 4/2004 | Johnson et al. |
| 2004/0111155 A1 | 6/2004 | Ferree |
| 2004/0186576 A1 | 9/2004 | Biscup et al. |
| 2004/0220580 A1 | 11/2004 | Johnson et al. |
| 2004/0220672 A1* | 11/2004 | Shadduck ................ 623/17.16 |
| 2004/0230198 A1 | 11/2004 | Manzi et al. |
| 2004/0267366 A1 | 12/2004 | Kruger |
| 2005/0010290 A1* | 1/2005 | Hawkins .................. 623/17.11 |
| 2005/0015150 A1 | 1/2005 | Lee |
| 2005/0055097 A1 | 3/2005 | Grunberg et al. |
| 2005/0154463 A1* | 7/2005 | Trieu ....................... 623/17.16 |
| 2005/0154465 A1 | 7/2005 | Trieu |
| 2005/0273178 A1* | 12/2005 | Boyan et al. ............ 623/23.74 |
| 2006/0247778 A1* | 11/2006 | Ferree et al. ............ 623/17.14 |
| 2006/0264965 A1 | 11/2006 | Shadduck et al. |
| 2007/0032874 A1* | 2/2007 | Lee et al. ................ 623/17.13 |

\* cited by examiner

INTERLOCKED MODULAR DISC NUCLEUS PROSTHESIS

RELATED APPLICATIONS

The present invention claims priority to U.S. Provisional Patent Application No. 60/660,107, entitled "MODULAR DISC PROSTHESIS," filed Mar. 9, 2005, U.S. Provisional Patent Application No. 60/685,332, entitled "SPINE DISC NUCLEUS II," filed May 24, 2005, and U.S. Provisional Patent Application No. 60/700,459, entitled "SPINE POLYMER PATENT," filed Jul. 19, 2005, the disclosures of which are hereby incorporated by reference. The present invention is also related to the co-pending application Ser. No. 11/372,477 filed concurrently herewith entitled, "RAIL-BASED MODULAR DISC NUCLEUS PROSTHESIS", a copy of which is attached hereto and the disclosure of which is hereby incorporated by reference.

FIELD OF THE INVENTION

The present invention relates generally to an implantable prosthesis for repairing damaged intervertebral discs. More particularly, the present invention relates to an interlocked modular disc nucleus prosthesis of predetermined size and shape.

BACKGROUND OF THE INVENTION

The spinal motion segment consists of a unit of spinal anatomy bounded by two vertebral bodies, including the two vertebral bodies, the interposed intervertebral disc, as well as the attached ligaments, muscles, and the facet joints. The disc consists of the end plates at the top and bottom of the vertebral bones, the soft inner core, called the nucleus and the annulus fibrosus running circumferentially around the nucleus. In normal discs, the nucleus cushions applied loads, thus protecting the other elements of the spinal motion segment. A normal disc responds to compression forces by bulging outward against the vertebral end plates and the annulus fibrosus. The annulus consists of collagen fibers and a smaller amount of elastic fibers, both of which are effective in resisting tension forces. However, the annulus on its own is not very effective in withstanding compression and shear forces.

As people age the intervertebral discs often degenerate naturally. Degeneration of the intervertebral discs may also occur in people as a result of degenerative disc disease. Degenerative disc disease of the spine is one of the most common conditions causing pain and disability in our population. When a disc degenerates, the nucleus dehydrates. When a nucleus dehydrates, its ability to act as a cushion is reduced. Because the dehydrated nucleus is no longer able to bear loads, the loads are transferred to the annulus and to the facet joints. The annulus and facet joints are not capable of withstanding their increased share of the applied compression and torsional loads, and as such, they gradually deteriorate. As the annulus and facet joints deteriorate, many other effects ensue, including the narrowing of the interspace, bony spur formation, fragmentation of the annulus, fracture and deterioration of the cartilaginous end plates, and deterioration of the cartilage of the facet joints. The annulus and facet joints lose their structural stability and subtle but pathologic motions occur between the spinal bones.

As the annulus loses stability it tends to bulge outward and may develop a tear allowing nucleus material to extrude. Breakdown products of the disc, including macroscopic debris, microscopic particles, and noxious biochemical substances build up. The particles and debris may produce sciatica and the noxious biochemical substances can irritate sensitive nerve endings in and around the disc and produce low back pain. Affected individuals experience muscle spasms, reduced flexibility of the low back, and pain when ordinary movements of the trunk are attempted.

Degeneration of a disc is irreversible. In some cases, the body will eventually stiffen the joints of the motion segment, effectively re-stabilizing the discs. Even in the cases where re-stabilization occurs, the process can take many years and patients often continue to experience disabling pain. Extended painful episodes of longer than three months often leads patients to seek a surgical solution for their pain.

Several methods have been devised to attempt to stabilize the spinal motion segment. Some of these methods include: heating the annular region to destroy nerve endings and strengthen the annulus; applying rigid or semi-rigid support members on the sides of the motion segment or within the disc space; removing and replacing the entire disc with a generally rigid plastic, articulating artificial device; removing and replacing the nucleus; and spinal fusion involving permanently fusing the vertebrae adjacent the affected disc.

Until recently, spinal fusion has generally been regarded as the most effective surgical treatment to alleviate back pain due to degeneration of a disc. While this treatment is often effective at relieving back pain, all discal motion is lost in the fused spinal motion segment. The loss of motion in the affected spinal segment necessarily limits the overall spinal mobility of the patient. Ultimately, the spinal fusion places greater stress on the discs adjacent the fused segment as these segments attempt to compensate for lack of motion in the fused segment, often leading to early degeneration of these adjacent spinal segments.

Current developments are focusing on treatments that can preserve some or all of the motion of the affected spinal segment. One of these methods to stabilize the spinal motion segment without the disadvantages of spinal fusion is total disc replacement. Total disc replacement is a highly invasive and technically demanding procedure which accesses the disc from an anterior or frontal approach and includes dividing the anterior longitudinal ligament, removing the cartilaginous end plates between the vertebral bone and the disc, large portions of the outer annulus and the complete inner nucleus. Then an artificial total disc prosthesis is carefully placed in the evacuated disc space. Many of the artificial total disc replacements currently available consist of a generally rigid plastic such as ultra high molecular weight polyethylene ("UHMWPE") as the nucleus that is interposed between two metal plates that are anchored or attached to the vertebral endplates. A summary of the history of early development and designs of artificial discs is set forth in Ray, "The Artificial Disc: Introduction, History and Socioeconomics," Chpt. 21, *Clinical Efficacy and Outcome in the Diagnosis of Low Back Pain*, pgs. 205-225, Raven Press (1992). Examples of these layered total disc replacement devices are shown, for example, in U.S. Pat. Nos. 4,911,718, 5,458,643, 5,545,229 and 6,533,818.

These types of artificial total discs have several disadvantages. First, because the artificial disc replacements are relatively large, they require relatively large surgical exposures to accommodate their insertion. The larger the surgical exposure, the higher the chance of infection, hemorrhage or even morbidity. Also, in order to implant the prosthetic, a large portion of the annulus must be removed. Removing a large portion of the annulus reduces the stability of the motion segment, at least until healing occurs around the artificial disc. Further, because the devices are constructed from rigid materials, they can cause serious damage if they were to displace from the disc space and contact local nerve or vascular tissues. Another disadvantage is that rigid artificial disc replacements do not reproduce natural disc mechanics.

An alternative to total disc replacement is nucleus replacement. Like an artificial disc prosthesis, these nucleus replacements are also inert, non-rigid, non-biological replacements. The procedure for implanting a nucleus replacement is less invasive than the procedure for a total disc replacement and generally includes the removal of only the nucleus and replacement of the nucleus with a prosthesis that may be elastically compressible and provide cushioning that mimics a natural disc nucleus. Examples of implants used for nucleus replacement include: U.S. Pat. Nos. 4,772,287, 4,904,260, 5,192,326, 5,919,236 and 6,726,721.

Nucleus replacements are intended to more closely mimic natural disc mechanics. To that end, some nucleus replacements utilize hydrogels because of their water imbibing properties that enable these replacements to expand in situ to permit a more complete filling of the evacuated nucleus cavity. However, there is usually a trade-off in that the more expansion the hydrogel achieves, the less structural support the end product can provide. As a result, many hydrogel nucleus disc replacements have generally adopted the use of some form of a jacket or fabric to constrain the hydrogel material. For example, the implant described in U.S. Pat. Nos. 4,772,287 and 4,904,260 consists of a block of hydrogel encased in a plastic fabric casing. The implant described in U.S. Pat. No. 5,192,326 consists of hydrogel beads enclosed by a fabric shell. Without the jacket or other form of constraint, the hydrogel is susceptible to displacement because of the slippery nature of the hydrogel. Unfortunately, the jacket or fabric shell will be subject to long term abrasive wear issues that could result in failure of the jacket or shell's ability to constrain the hydrogel and thus the hydrogel may be subject to displacement.

Another approach to nucleus replacement involves implantation of a balloon or other container into the nucleus, which is then filled with a biocompatible material that hardens in situ. Examples of this in situ approach to nucleus replacement include U.S. Pat. Nos. 6,443,988 and 7,001,431. One of the problems with this approach is that the chemical hardening process is exothermic and can generate significant amounts of heat that may cause tissue damage. In addition, there is a possibility that the balloon may rupture during expansion, causing leakage of material into the disc cavity and surrounding tissues, which may cause undesirable complications.

Another technique for nucleus replacement involves implanting a multiplicity of individual support members, such as beads, one at a time in the evacuated disc nucleus cavity until the cavity is full. Examples of this approach include U.S. Pat. Nos. 5,702,454 and 5,755,797. Because each of the individual support members or beads is relatively small, there is a possibility that one or more of the individual support members or beads may extrude out of the evacuated disc nucleus cavity. From a mechanical perspective, this technique is limited in the ability to produce consistent and reproducible results because the location and interaction of the multiplicity of beads or support members is not controlled and the beads or support members can shift during and after implantation.

Accordingly, there is a need for a nucleus prosthesis that may be inserted using a minimally invasive procedure and that mimics the characteristics of a natural disc.

SUMMARY OF THE INVENTION

The present invention provides a method and apparatus for repairing a damaged intervertebral disc nucleus in a minimally invasive manner utilizing a modular disc nucleus prosthesis. The modular disc prosthesis preferably comprises at least three modular segments. This configuration allows the prosthesis to be adapted for implantation through various surgical approaches, although the preferred method is the posterolateral ("posterior") approach where the disc is accessed through the patient's back. In one embodiment, each modular segment includes an inner core and an outer shell. The modular segments are selectively interlockable in situ with each other. The modular segments form an implanted unitary device that closely mimics the geometry of the disc nucleus cavity.

In one embodiment, a modular disc nucleus prosthesis that is adapted to be implanted in an evacuated disc nucleus space includes at least three modular segments each having a width defined by opposing sides, a proximal end, and a distal end. The modular segments are selectively interlockable with each other such that the prosthesis has an extended configuration and an implanted configuration. In the extended configuration the proximal end of one side of an outer modular segment is operably positioned proximate the distal end of one of the sides of an intermediate modular segment and the distal end of one side of another outer modular segment is operably positioned proximate the proximal end of another of the sides of an intermediate modular segment. In the implanted configuration the modular segments are positioned within the evacuated nucleus disc space in a generally side by side relation with the proximal ends of each modular segment adjacent one another and the distal ends of each modular segment adjacent one another so as to define a unitary body having a generally continuous periphery in which an overall width of the modular segments generally corresponds to a width of the evacuated disc nucleus cavity.

In one embodiment, each modular segment comprises an inner core and an outer shell. Outer shells of modular segments are preferably comprised of a polymeric material. In one embodiment, the inner cores of the modular segments are comprised of polyvinyl alcohol (PVA), which can be insert molded into the polymer outer shell. This softens the compression modulus of the modular disc prosthesis, allowing the device to more closely mimic the properties of a natural disc nucleus. In addition, PVA will cause the prosthesis to swell a small amount once inside the body, allowing the device to more fully fill the disc nucleus space.

In another embodiment, each modular segment comprises an inner core and an outer shell. The inner core includes structure that allows adjacent modular segments to mate with one another. The outer shell substantially surrounds the inner core, except for the sides having the mating structure. In one embodiment, the inner core of each modular segment and the outer shell of each modular segment are made of polymers of different durometers. In this embodiment, the inner core of each modular segment preferably has a compressive modulus from about 70-100 MPa and the outer shell of each modular segment has a compressive modulus from about 6-20 MPa. The use of a harder inner core and softer outer shell as part of an integrated unitary implanted device permits the modular prosthesis of the present invention to more closely mimic the stress response of a biological disc nucleus while simultaneously permitting effective operation of the slidable relationship between adjacent modular segments.

Another aspect of the present invention provides a method for implanting a modular disc nucleus prosthesis. The method is minimally invasive because the modular disc prosthesis is implanted incrementally, so the device can be implanted through an annulotomy much smaller than the size of the implanted configuration of the device. To implant modular disc prosthesis, the first modular segment is introduced into the patient's disc space and is placed partway into the disc nucleus space. The second modular segment is then attached to the first modular segment. When the first modular segment is mostly inserted into the disc nucleus space the second modular segment is slid up partway into the disc space and the third modular segment is attached to the second modular segment. The first modular segment is completely inserted at this point. The second modular segment is then extended into position along side of the first modular segment and is locked into place in the disc nucleus space. Finally, the third modular segment is inserted completely into the disc nucleus space and is locked in place with the other modular segments. The final implanted side by side configuration of modular segments of the modular disc prosthesis is sized and shaped to mimic the natural disc nucleus. It will be recognized that there may be more than three modular segments and that the modular segments may be attached to one another before or during the operation to form the expanded configuration as described.

Another aspect of the present invention provides an insertion tool for inserting the modular segments of modular disc nucleus prosthesis and interlocking the modular segments in situ. Insertion tool has a distal end having a mechanism that selectively engages and releases one or more modular segments and a proximal end having a means to activate the engagement and release mechanism. The distal end of insertion tool may also include a means to align a modular segment being inserted with one already positioned in the disc space.

BRIEF DESCRIPTION OF THE DRAWINGS

The invention may be more completely understood in consideration of the following detailed description of various embodiments of the invention in connection with the accompanying drawings, in which.

DETAILED DESCRIPTION OF THE DRAWINGS

Figure 1:
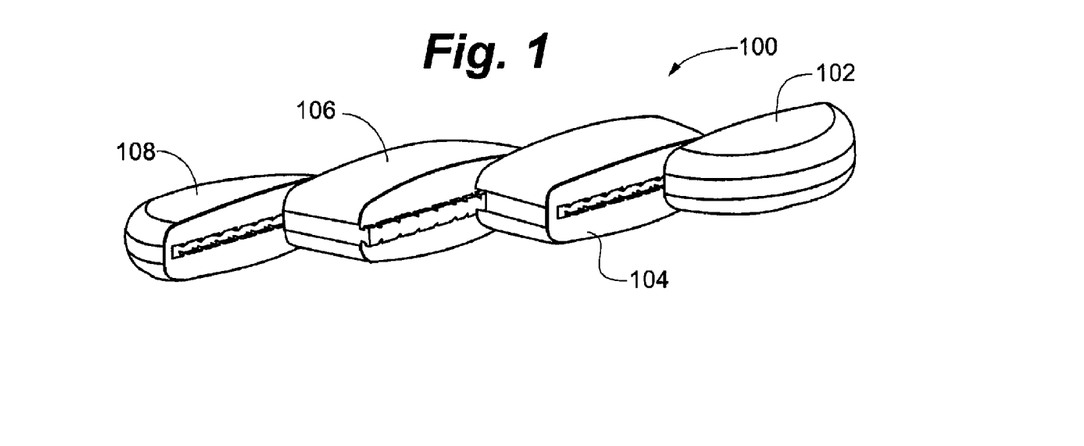
FIG. 1 is a perspective view of a modular disc prosthesis according to the preferred embodiment of the present invention.
Figure 2:
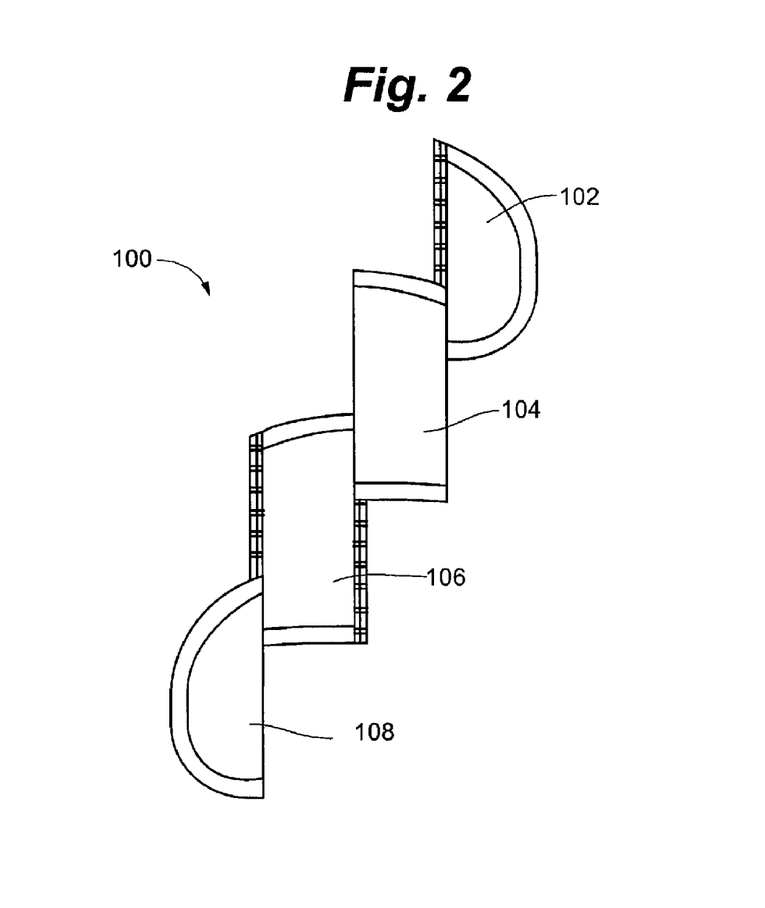
FIG. 2 is a top view of a modular disc prosthesis according to the preferred embodiment of the present invention.

Referring to FIGS. 1 and 2, there can be seen a modular disc prosthesis 100 according to the preferred embodiment of the present invention. In this embodiment, modular disc prosthesis 100 comprises first 102, second 104, third 106, and fourth 108 interlocking modular segments. One of skill in the art will recognize that in alternate embodiments the preferred embodiment can be easily modified to comprise greater or fewer modular segments, as long as there are at least three modular segments for a posterolateral approach and at least two modular segments for an anteriolateral approach.

Figure 3A:
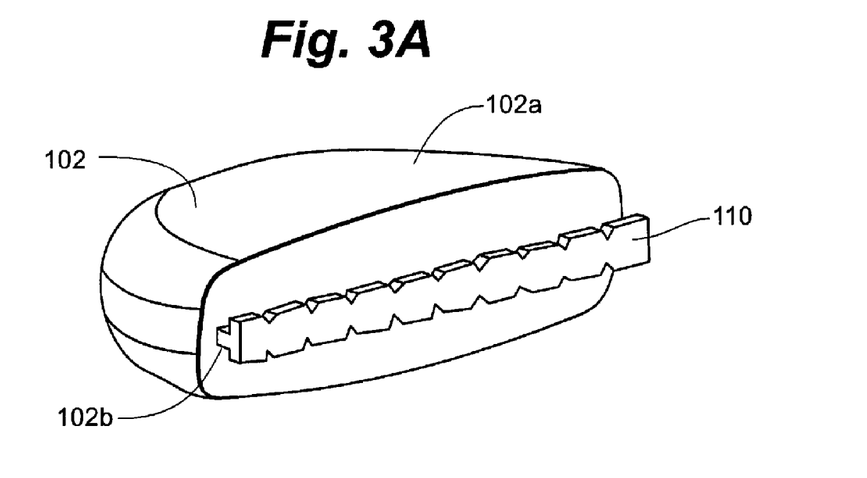
FIG. 3A is a perspective view of a first modular segment according to the preferred embodiment of the present invention.
Figure 3B:
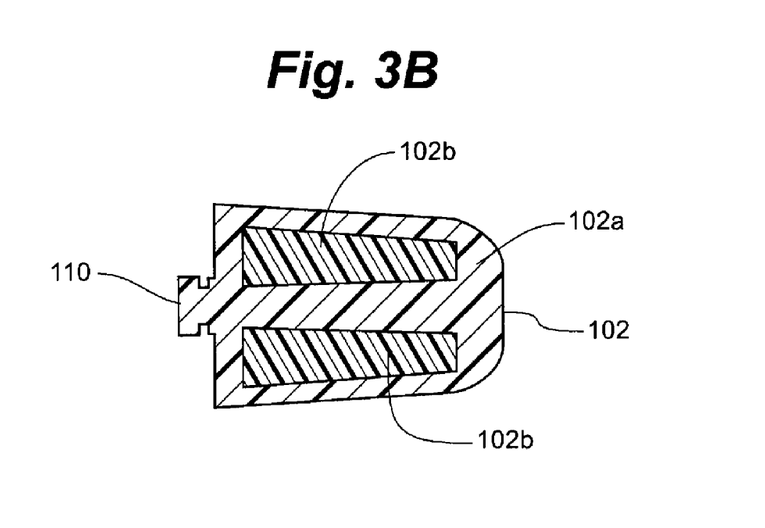
FIG. 3B is a cross sectional view of a first modular segment according to the preferred embodiment of the present invention.

Referring now to FIGS. 3A-3B there can be seen first modular segment 102 of modular disc prosthesis 100 according to the preferred embodiment of the present invention. First modular segment 102 is preferably comprised of an outer shell 102a and an inner core 102b. Inner core 102b further includes a locking slide 110 for interlocking with an adjacent modular segment.

Figure 4:
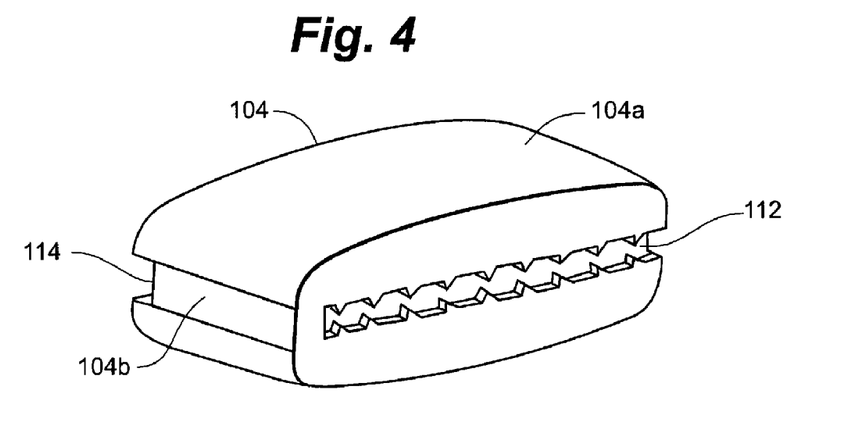
FIG. 4 is a perspective view of a second modular segment according to the preferred embodiment of the present invention.

Second modular segment 104 according to the preferred embodiment of the present invention is depicted in FIG. 4. Second modular segment 104 is comprised of an outer shell 104a and an inner core 104b. Inner core 104b further includes first 112 and second 114 slots into which locking slides of adjacent modular segments are inserted.

Figure 5:
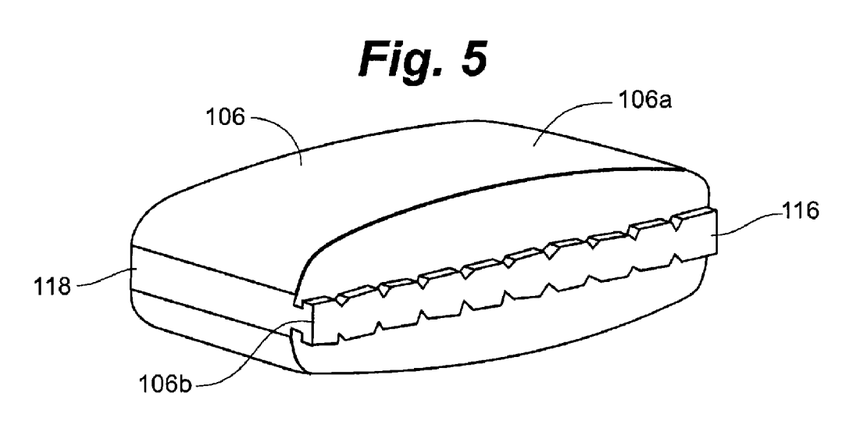
FIG. 5 is a perspective view of a third modular segment according to the preferred embodiment of the present invention.

Referring to FIG. 5, third modular segment 106 of the preferred embodiment of modular disc prosthesis 100 is shown. Third modular segment 106 is comprised of an outer shell 106a and an inner core 106b. Inner core 106b further includes first 116 and second 118 locking slides for insertion into slots in adjacent modular segments.

Figure 6:
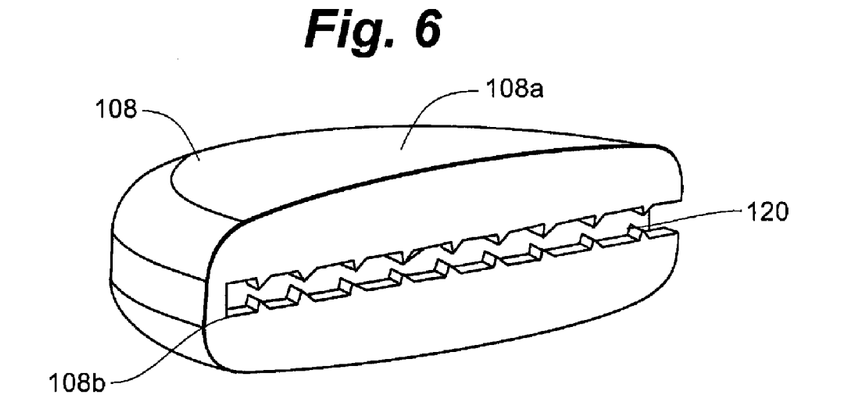
FIG. 6 is a perspective view of a fourth modular segment according to the preferred embodiment of the present invention.

The fourth modular segment 108 according to the preferred embodiment of the present invention is shown in FIG. 6. Fourth modular segment 108 is comprised of an outer shell 108a and an inner core 108b. Inner core 108b further includes a slot 120 for connecting to an adjacent modular segment.

As can be seen from the above description and the drawings, each modular segment 102, 104, 106, 108 is unique. The two outermost modular segments 102 and 108 have interlocking structure defined on only an inner facing side, whereas the intermediate modular segments 104 and 106 have interlocking structure defined on both side of the width of each module. The unique configuration of each module assures that the order of insertion of the modular segments cannot be mixed up and the proper number of modular segments is used. The four part design comes packaged sterile and ready for assembly at the surgical site. In alternate embodiments, modular segments may be of a uniform design (for example, a slot on one side and a locking slide on the other) in order to allow for the surgeon to freely add or subtract from the total number of modular segments or to select an intermediate modular segment of differing widths to change the size of modular disc prosthesis to better accommodate the disc nucleus space in a particular procedure.

Figure 7:
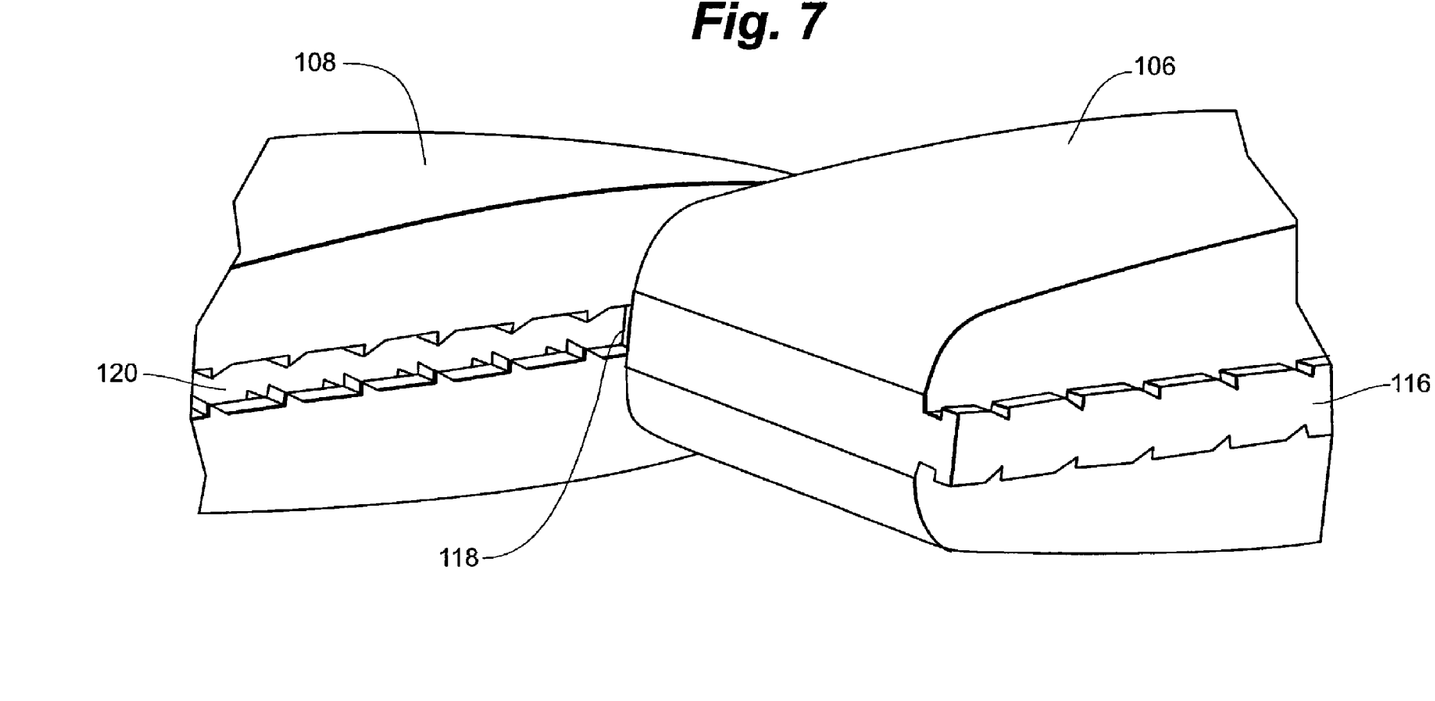
FIG. 7 is a partial view of a modular disc prosthesis according to the preferred embodiment of the present invention.

As can be seen in FIG. 7, modular segments 102, 104, 106, 108 are capable of interlocking with one another by inserting locking slides 110, 116, 118 into slots 112, 114, 120. In the preferred embodiment, locking slides 110, 116, 118 and slots 112, 114, 120 have a tongue-in-groove design. Interlocking may be accomplished with ridges, dovetail, ratchet and pawl or any other suitable mechanical interface method. Interlocking may also be complimented by or entirely accomplished by material interface such as by forming the interlocking interface of materials that are hygroscopic and swell in situ or by forming a chemical bond across the interface.

Interlocking may be strengthened by providing locking elements, such as barbs, molded along the locking slides with corresponding locking ridges molded on the edges of slots. In an embodiment of the present invention, the disc nucleus device includes at least one bidirectional locking element to prevent forward and/or backward motion of the components. In another embodiment, the disc nucleus prosthesis may include at least two unidirectional locking elements. Wherein at least one of the locking elements prevents forward movement of the components and at least one of the other unidirectional locking elements prevents backward movement of the components. A ratchet release tool or other similar tool may be provided in case separation of modular segments is desired once they are locked together. One of skill in the art will recognize that modular segments can interlock through a variety of other means. In addition, modular segments may also be provided with an end block to ensure flush alignment between modular segments.

In the preferred embodiment, modular disc prosthesis 100 is molded from elastomeric biomaterials, preferably polyurethane. Inner cores 102b, 104b, 106b, 108b are made from a hard durometer polyurethane, such as a polyurethane with a Shore D hardness of about 45 or above and compressive modulus in the range of about 70 to 100 MPa. Outer shells 102a, 104a, 106a, 108a are made from a softer durometer polyurethane, such as a polyurethane with a Shore A hardness ranging from about 40 to 80 and a compressive modulus in the range of about 6 to 20 MPa.

In the preferred embodiment, the two different durometer polyurethanes may be co-polymerized to create a chemical bond between the two portions of each modular segment 102, 104, 106, 108. In alternate embodiments, other polymers such as PEEK, polyethylene, silicones, acrylates, nylon, polyacetyls, and other similar biocompatible polymers may be used for the inner cores or the outer shells.

In an alternative embodiment, inner core 102b, 104b, 106b, 108b of modular segments 102, 104, 106, 108 is comprised of polyvinyl alcohol (PVA). PVA may be insert molded into the polyurethane shell. The PVA takes on much more water than the polyurethane, which serves two advantages. First, this softens the compression modulus of modular disc prosthesis 100, allowing the device to more closely mimic the properties of a natural disc nucleus. Second, it will swell the prosthesis 100 a small amount once inside the body, allowing the device to more fully fill the disc nucleus space. Those of skill in the art will understand how to select a PVA of appropriate hydrophilic characteristic to adjust the resultant compressive modulus of the prosthesis to a physiologically acceptable value. In alternate embodiments, the inner core may be comprised of any other suitable hygroscopic material.

In the preferred embodiment, the modular disc nucleus prosthesis is deformable in response to normal physiological forces of 30 to 300 pounds. Because of this deformability, the prosthesis produces a physiologically appropriate amount of loading on the end plates of the intervertebral disc. As a result, the end plates will not excessively deform over time and ultimately conform to the contours of the implant as is the case with many more rigid disc nucleus replacement implants.

The modular disc nucleus prosthesis may be introduced through an access tube that is inserted partially into the disc nucleus space. Access tube is at least 3 inches long and preferably about 6 inches long. It should be noted that although the insertion of modular disc prosthesis is described in relation to a preferred four-segment embodiment, embodiments having any other number of segment s would be inserted in a similar fashion.

An insertion tool may be used to aid in the insertion and positioning of the modular prosthesis. Such a tool has a distal end that selectively engages and releases the modular segments and a proximal end containing a means to activate the engagement and release mechanism. The engagement method of the insertion tool may include a full or partial sleeve that provides an interference fit with the outer surface of the modular segments, a rod possessing a tip that can be expanded to interlock in a corresponding cavity within each modular segment, two or more rods with shaped or angled tips that can be inserted and opposed into corresponding cavities within each modular segment, or other similar means apparent to one skilled in the art. The distal end of the insertion tool may also possess a wire, rod, rail, or other means to align a modular segment being inserted with one already positioned at least partly within the disc space. The insertion tool may be made out of any combination of plastics, metals, ceramics, or the like.

Figure 8:
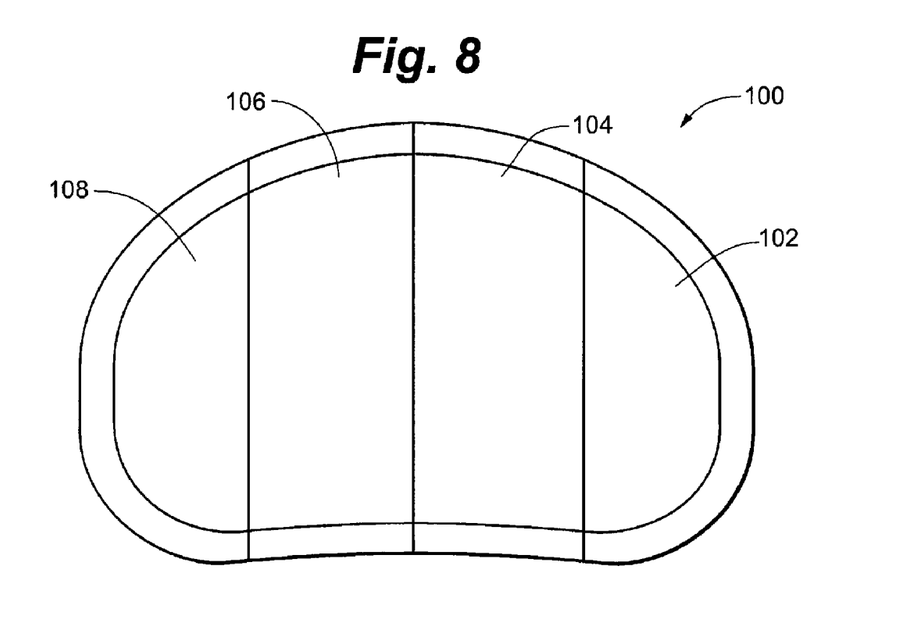
FIG. 8 is a top view of a modular disc prosthesis according to the preferred embodiment of the present invention.

Upon inserting the access tube into the disc nucleus space, first modular segment 102, as shown in FIGS. 1 and 2, is inserted part way into the disc space using a first insertion tool. The distal end of the second modular segment 104 is then attached to the proximal end of the first modular segment 102 by sliding slot 112 onto locking slide 110 with a second insertion tool. When first modular segment 102 is preferably approximately 80% inserted into the disc nucleus space, the second modular segment 104 is transposed along the locking slide 110 of first modular segment 102 partway into the disc nucleus space and the distal end of the third modular segment 106 is attached to the proximal end of the second modular segment 104 by sliding locking slide 116 into slot 114 with a third insertion tool. First modular segment 102 is completely inserted at this point and is released from the first insertion tool. Second modular segment 104 is then extended into position along side of first modular segment 102, is locked into place in the disc nucleus space and is released from second insertion tool. Third modular segment 106 is now partway in the disc nucleus space and the distal end of fourth modular segment 108 is attached to the proximal end of third modular segment 106 by sliding slot 120 onto locking slide 118 with a fourth insertion tool. Third modular segment 106 is then completely inserted and locked into place and is released from third insertion tool. Finally, fourth modular segment 108 is inserted completely into the disc nucleus space, locked in place with the other modular segments, and released from fourth insertion tool. The final, locked configuration of modular disc prosthesis 100 of this embodiment is shown in FIG. 8.

In another embodiment, first modular segment is engaged by a first insertion tool and fully inserted into the nucleus cavity. Second modular segment is then attached to first modular segment using a second insertion tool and is fully inserted into the nucleus cavity. Subsequent modular segments are then attached in the same manner until the modular prosthesis is fully assembled. Alternatively, the insertion tool used with any of the embodiments of the present invention may be designed to engage two or more modular segments simultaneously to avoid requiring multiple insertion tools to perform the implantation procedure.

Alternatively, modular disc prosthesis may be implanted using an anterior lateral approach. An anterior lateral approach allows for a larger insertion opening to be used while still being minimally invasive. In this approach, the disc is accessed from the patient's side through the psoas muscle, which avoids major nerve and vascular tissues, and may be used in the presence of medical conditions mitigating against the posterior approach. This approach is essentially oriented 90° from the posterior approach.

The prosthesis consists of preformed components that are under direct surgeon control until the device is completely formed, thus, there is little chance of dislocation of the components as the components are inserted. The ability to control the components during insertion is an advantage over devices that employ individual support members, such as beads, which once inserted are beyond the surgeon's control and may move about in the evacuated disc space. Because the components of the present invention remain under the surgeon's direct control, the surgeon is able to place the components more precisely in the evacuated disc space with less chance of the components moving into an undesirable position during insertion of the device.

Further, the ability to predetermine the size of the modular disc prosthesis also allows for the nucleus cavity to be more completely filled and provides a greater degree of control over the uniformity of the stress response of the implant as compared to other kinds of minimally invasive implants. Because the stress response of the implant may be controlled, even with an incompetent posterior wall, the prosthesis should remain stable. The ability to tailor the size of the prosthesis and completely fill the nucleus cavity also prohibits the prosthesis from dislodging out of the nucleus cavity after the device is completely implanted as can happen with some hydrogel block implants.

Figure 9:
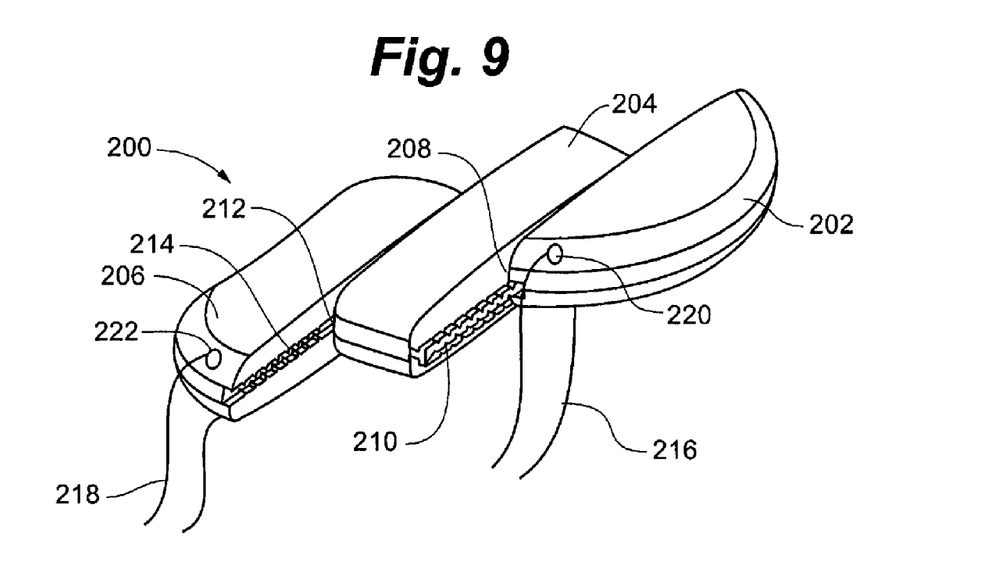
FIG. 9 is a perspective view of a modular disc prosthesis according to an alternate embodiment of the present invention.
Figure 10:
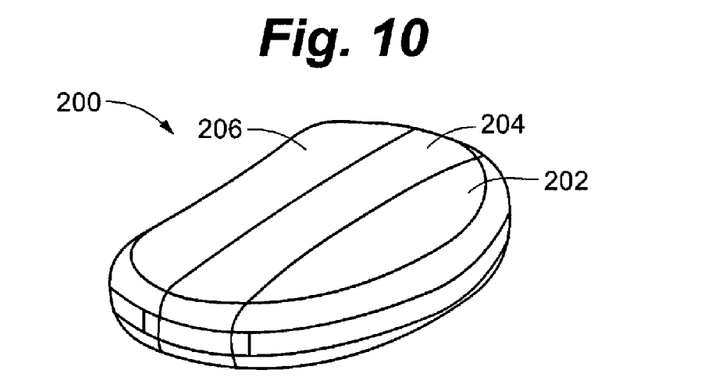
FIG. 10 is a perspective view of a modular disc prosthesis according to an alternate embodiment of the present invention.

Referring now to FIGS. 9 and 10 there can be seen an alternate embodiment of modular disc prosthesis 200. Modular disc prosthesis 200 is a three piece implant with tethers 216, 218 to help align the device. Modular disc prosthesis 200 comprises a first modular segment 202 with a slot 208 formed therein, a second modular segment 204 with first 210 and second 212 locking slides, and a third modular segment 206 having a slot 214. Modular disc prosthesis 200 further includes tethers 216, 218 that are threaded through holes 220, 222 in first modular segment 202 and third modular segment 206. One of skill in the art will recognize that the number and location of tethers 216, 218 may vary and that tethers may be used with modular disc prosthesis having different numbers of modular segments.

In an alternate embodiment, the outer shell of the modular disc nucleus prosthesis may be modified to provide for elution of medicants. Such medicants may include analgesics, antibiotics, antineoplastics or bioosteologics such as bone growth agents. While motion preservation is generally a principle goal in nucleus replacement, in certain indications it may be desirable to promote some bony fusion. Such indications may include nuclear replacements in the cervical spine.

The solid polymer outer shell of the modular disc nucleus prosthesis may provide for better and more controllable elution rates than some hydrogel materials. In an alternate embodiment, the modular disc nucleus prosthesis may include different elution rates for each polymer material. This would allow for varying elution rates for different medicants.

Various modifications to the disclosed apparatuses and methods may be apparent to one of skill in the art upon reading this disclosure. The above is not contemplated to limit the scope of the present invention, which is limited only by the claims below.

The invention claimed is:

1. A modular disc prosthesis that is adapted to be implanted in an evacuated disc nucleus space from a generally posterior approach, the prosthesis comprising:
    at least three modular segments, each modular segment having a width defined by opposing sides, a proximal end, and a distal end, the modular segments being selectively interlockable with each other such that the prosthesis has:
    an extended configuration in which the proximal end of one side of an outer modular segment is operably positioned proximate the distal end of one of the sides of an intermediate modular segment and the distal end of one side of another outer modular segment is operably positioned proximate the proximal end of another of the sides of an intermediate modular segment; and
    an implanted configuration in which the modular segments are positioned within the evacuated nucleus disc space in a generally side by side relation with the proximal ends of each modular segment adjacent one another and the distal ends of each modular segment adjacent one another so as to define a unitary body having a generally continuous periphery in which an overall width of the modular segments generally corresponds to a width of the evacuated nucleus disc space;
    wherein each modular segment comprises an inner core and an outer shell, the inner core including structure on at least one side that selectively interlocks with corresponding structure on at least one side of an adjacent modular segment and the outer shell substantially surrounds the inner core except for the sides having the structure that selectively interlocks adjacent modular segments;
    wherein, the inner core of each modular segment and the outer shell of each modular segment are made of polymers of different durometers; and
    the inner core of each modular segment having a compressive modulus from about 70-100 Mpa and the outer shell of each modular segment having a compressive modulus from about 6-20 MPa.

* * * * *